US007503900B2

(12) United States Patent
Goswami

(10) Patent No.: US 7,503,900 B2
(45) Date of Patent: Mar. 17, 2009

(54) KINEMATIC QUANTIFICATION OF GAIT ASYMMETRY BASED ON BILATERAL CYCLOGRAMS

(75) Inventor: Ambarish Goswami, Fremont, CA (US)

(73) Assignee: Honda Motor Co., Ltd., Tokyo (JP)

( * ) Notice: Subject to any disclaimer, the term of this patent is extended or adjusted under 35 U.S.C. 154(b) by 426 days.

(21) Appl. No.: 10/613,116

(22) Filed: Jul. 3, 2003

(65) Prior Publication Data

US 2005/0004495 A1    Jan. 6, 2005

(51) Int. Cl.
 *A61B 5/103* (2006.01)
(52) U.S. Cl. ..................................... 600/595
(58) Field of Classification Search ................ 600/595, 600/587
 See application file for complete search history.

(56) References Cited

U.S. PATENT DOCUMENTS

| | | | | | |
|---|---|---|---|---|---|
| 4,813,436 | A | * | 3/1989 | Au .............................. | 600/592 |
| 5,957,870 | A | * | 9/1999 | Yamato et al. .............. | 600/592 |
| 6,010,465 | A | * | 1/2000 | Nashner ...................... | 600/595 |
| 6,152,890 | A | * | 11/2000 | Kupfer et al. ............... | 600/595 |
| 6,290,658 | B1 | * | 9/2001 | Kolich ......................... | 600/595 |
| 6,895,341 | B2 | * | 5/2005 | Barrey et al. ................. | 702/32 |
| 2004/0059264 | A1 | * | 3/2004 | Nishibe et al. .............. | 600/587 |

FOREIGN PATENT DOCUMENTS

| | | |
|---|---|---|
| JP | 9-237351 | 9/1997 |
| JP | 2002-65641 | 5/2002 |
| WO | WO 01/56470 | * 8/2001 |

OTHER PUBLICATIONS

Oberg et al; An Investigation of Kinematic and Kinetic Variables forthe Description of Prosthetic Gait using the ENOCH System; 1982; Prosthetics and Orthotics International, 6; p. 43-47.*
Notification of Transmittal of the International Search Report and The Written Opinion of the International Searching Authority, or the Declaration, PCT/JP2004/009879, Oct. 19, 2004.
Grieve, D.W., *Gait Patterns and the Speed of Walking*, Bio-Medical Engineering, vol. 3, No. 3, Mar. 1968, pp. 119-122.
Hershler, C. et al., *Angle-Angle Diagrams in the Assessment of Locomotion*, American Journal of Physical Medicine, vol. 59, No. 3, Jun. 1980, pp. 109-125.
Pierotti, S.E. et al., *Are Leg Electromyogram Profiles Symmetrical?*, Journal of Orthopaedic Research, vol. 9, No. 5, Sep. 1991, pp. 720-729.

(Continued)

*Primary Examiner*—Max Hindenburg
*Assistant Examiner*—H. Q. Nguyen
(74) *Attorney, Agent, or Firm*—Fenwick & West LLP; Mark E. Duell

(57) ABSTRACT

Kinematic quantification of gait asymmetry is achieved by plotting the values of the angles of corresponding joints and then comparing the resulting figure to the figure that would have been produced based on a perfectly symmetrical gait. The comparison is based on geometric characteristics that are calculated based on the figures.

17 Claims, 23 Drawing Sheets

OTHER PUBLICATIONS

Robinson, R. O. et al., *Use of Force Platform Variables to Quantify the Effects of Chiropractic Manipulation on Gait Symmetry*, Journal of Manipulative and Physiological Therapeutics, vol. 10, No. 4, Aug. 1987, pp. 172-176.

Sadeghi, H. et al., *Functional Gait Asymmetry in Able-Bodied Subjects*, Human Movement Science, 16 (1997), pp. 243-258.

Jain, A. K., *Fundamentals of Digital Image Processing*, 1989 by Prentice-Hall, Inc., Englewood Cliffs, U.S., pp. 377-381, 392-394.

Sadeghi, Heydar, et al., "Symmetry and Limb Dominance in Able-Bodied Gait: a Review", Gait & Posture, Sep. 2000, pp. 34-45, 12(1), Elsevier Science B.V.

Goswami, Ambarish, "Kinematic Quantification of Gait Symmetry Based on Bilateral Cyclograms", International Society of Biomechanics XIXth Congress: The Human Body in Motion, Jul. 6-11, 2003, CD ROM: Abstracts and Proceedings, University of Otago, Dunedin, New Zealand.

Goswami, Ambarish, "A New Gait Parameterization Technique by Means of Cyclogram Moments: Application to Human Slope Walking", Gait & Posture, Aug. 1998, pp. 15-36, 8(1), Elsevier Science B.V.

* cited by examiner

| Time (seconds) | Left Knee (degrees) | Right Knee (degrees) |
| --- | --- | --- |
| 0 | 40.487 | 12.31 |
| 0.0167 | 32.837 | 12.101 |
| 0.0333 | 25.791 | 12.288 |
| 0.05 | 19.811 | 13.285 |
| 0.0667 | 15.156 | 13.93 |
| 0.0833 | 12.546 | 15.288 |
| 0.1 | 11.87 | 16.73 |
| 0.1167 | 12.628 | 18.95 |
| 0.1333 | 14.496 | 21.445 |
| 0.15 | 17.234 | 25.199 |
| 0.1667 | 19.871 | 29.939 |
| 0.1833 | 23.218 | 35.602 |
| 0.2 | 26.277 | 41.844 |
| 0.2167 | 28.937 | 48.608 |
| 0.2333 | 30.813 | 55.085 |
| 0.25 | 31.313 | 60.789 |
| 0.2667 | 30.925 | 65.489 |
| 0.2833 | 29.678 | 69.101 |
| 0.3 | 28.191 | 71.574 |
| 0.3167 | 26.359 | 72.791 |
| 0.3333 | 24.401 | 73.12 |
| 0.35 | 22.228 | 72.323 |
| 0.3667 | 20.526 | 70.646 |
| 0.3833 | 18.333 | 68.254 |
| 0.4 | 16.855 | 64.841 |
| 0.4167 | 15.459 | 60.875 |
| 0.4333 | 14.049 | 56.194 |
| 0.45 | 12.782 | 51.019 |
| 0.4667 | 11.898 | 44.928 |

Figure 3a

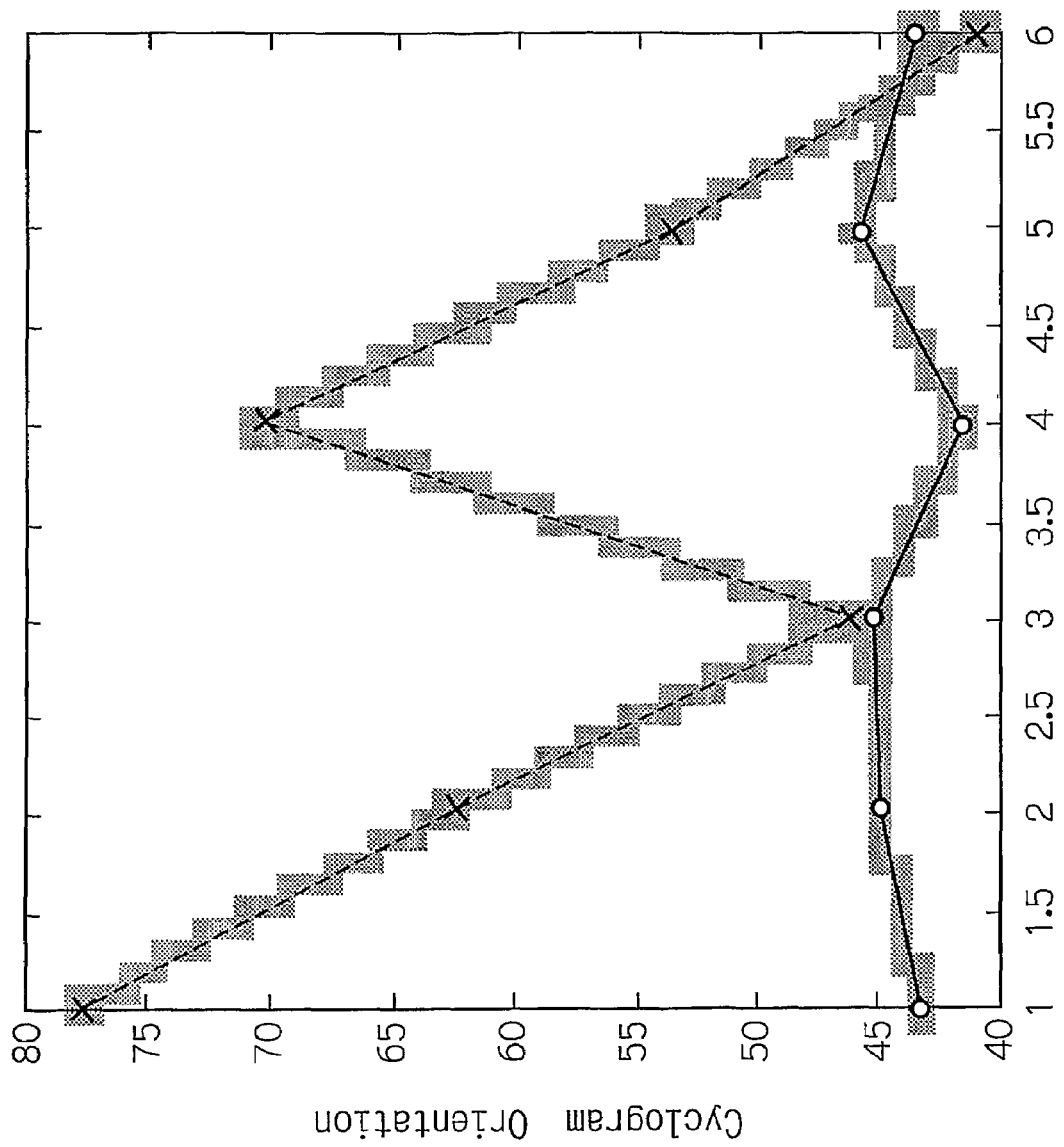

KINEMATIC QUANTIFICATION OF GAIT ASYMMETRY BASED ON BILATERAL CYCLOGRAMS

BACKGROUND OF THE INVENTION

1. Field of the Invention

This invention relates generally to analyzing gait symmetry, and more specifically, to quantifying gait asymmetry to determine deviation of actual gait from perfectly symmetrical gait.

2. Background Art

Gait asymmetry generally refers to the extent to which the two sides of the body behave differently during a walk cycle. Symmetry is considered to be an important indicator of healthy gait, and it is one of the first casualties of a gait pathology. Gait symmetry can be compromised due to various factors such as limb asymmetry, injury, use of prosthesis, stroke, cerebral palsy, and other mobility-affecting diseases.

Symmetry can be measured through virtually any measurable or computable gait variable. The value of the gait variable is measured or computed for one side of the body and then for the other side of the body, for a corresponding feature. One may use kinematic variables such as step period and step length or individual joint positions or velocities at specific gait events. Comparison between left and right foot trajectories is also a kinematic approach. Kinetic variables, on the other hand, involve acceleration, force, moment, energy, and power. Analyzing entire trajectories or specific discrete values of joint moment and segment power fall under this category. Symmetry can also be studied by comparing the ground reaction force profiles under the individual feet.

Among the existing gait symmetry quantifiers, algebraic indices and statistical parameters represent two major classes. Algebraic indices include the so-called symmetry index and the ratio index, both comparing bilateral variables such as step period or step length. Notwithstanding their successful use in some cases, both of the algebraic quantifiers suffer from major limitations. For example, since the indices report differences against their average values, if a large asymmetry is present, the average value does not correctly reflect the performance of either limb. Also, parameters that have large values but relatively small inter-limb differences will tend to lower the index and reflect symmetry. Additionally, these parameters depend on discrete variables and are thus unable to reflect the asymmetry as it evolves over a complete gait cycle.

Statistical techniques, such as paired t-tests and principal component analysis, and parameters, such as correlation coefficients, coefficients of variation, and variance ratios, have also been used to measure gait asymmetry. While the statistical parameters do not suffer from the limitations of the algebraic indices, their computation is more involved and their interpretation perhaps less transparent.

Despite the broad agreement in the fundamentals of what constitutes symmetry, there is yet to emerge a consensual objective measure of gait symmetry among the researchers. For a comprehensive review of the background and state of the art of gait symmetry research, see Symmetry and Limb Dominance in Able-Bodied Gait: A Review, H. Sadeghi, P. Allard, F. Prince, H. Labelle, Gait & Posture 12:34-45 (2000).

What is needed is a method to quantify gait asymmetry that overcomes the limitations of algebraic indices while also being less computationally involved and easier to interpret than statistical techniques and parameters.

SUMMARY OF THE INVENTION

The present invention provides a method for quantifying asymmetry of body movement. In one embodiment, the movement is walking, and the asymmetry concerns the angles of corresponding joints such as the left and right ankles, left and right knees, and left and right hips. In another embodiment, the quantification is based on characteristics of bilateral cyclograms formed from synchronized data.

BRIEF DESCRIPTION OF THE FIGURES

The invention is illustrated by way of example, and not by way of limitation, in the figures of the accompanying drawings in which like reference numerals refer to similar elements.

FIG. 3a illustrates a table of experimental data.

FIGS. 4a-l illustrate synchronized bilateral hip cyclograms of two sets of experimental subjects: "normal" subjects and subjects with gait pathologies.

FIG. 5b illustrates a graph of the orientations of the synchronized bilateral hip cyclograms in FIGS. 4a-l.

DETAILED DESCRIPTIONS OF THE PREFERRED EMBODIMENTS

Figure 1:
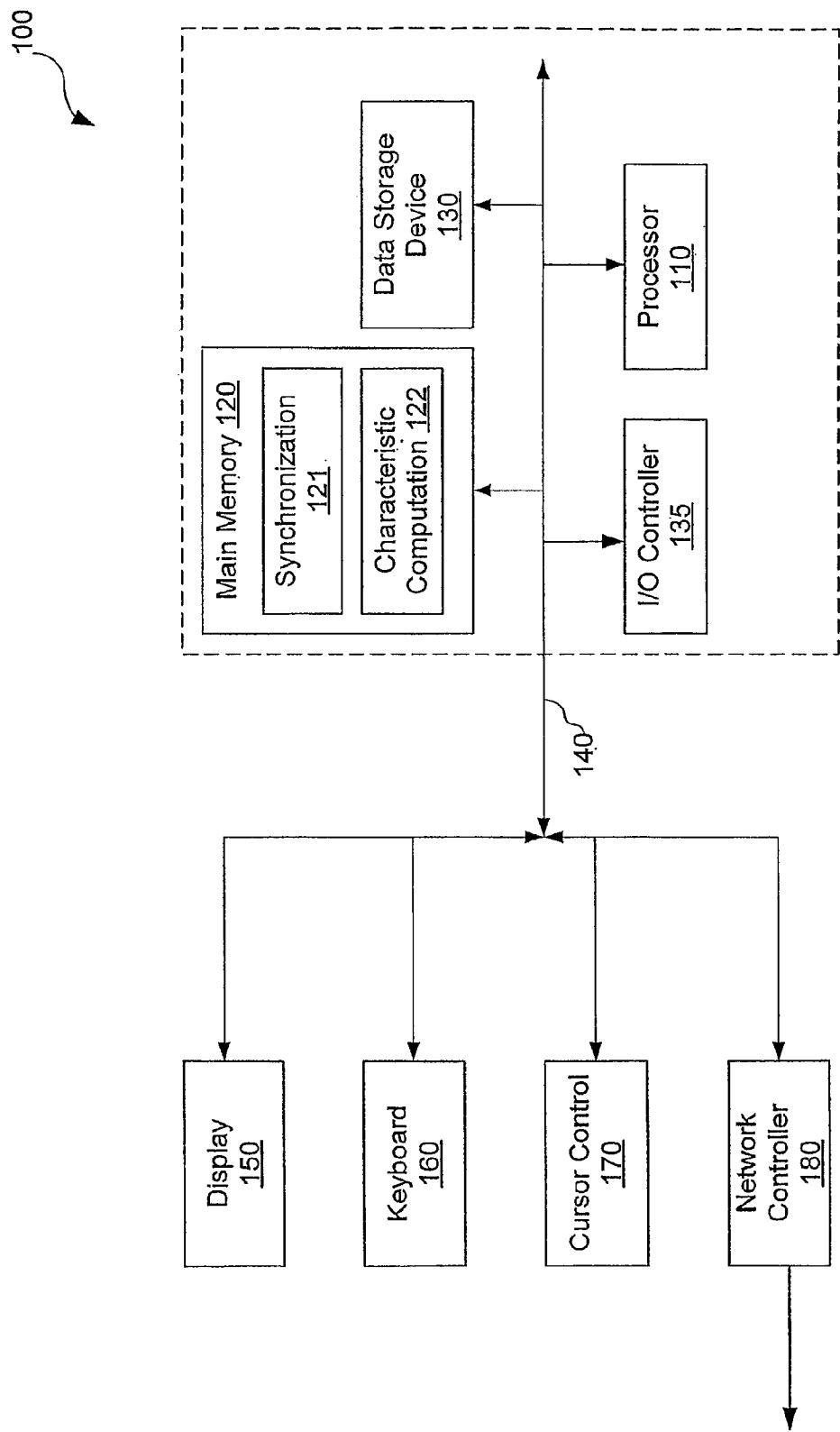
FIG. 1 illustrates a block diagram overview of one embodiment of a system for quantifying gait asymmetry.

FIG. 1 illustrates a block diagram of one embodiment of a system for quantifying gait asymmetry. System 100 preferably includes a processor 110, a main memory 120, a synchronization module 121, a characteristic computation module 122, an I/O controller 135, a data storage device 130, and a network controller 180, all of which are communicatively coupled to a system bus 140.

Main memory 120 stores instructions and/or data that are executed by processor 110. The instructions and/or data comprise code for performing any and/or all of the techniques described herein. Main memory 120 is preferably a dynamic random access memory (DRAM) device, a static random access memory (SRAM) device, or some other memory device known in the art. The synchronization module 121 and the characteristic computation module 122 will be discussed below.

The data storage device 130 stores data and instructions for the processor 110. Examples of the data storage device 130 are one or more of a hard disk drive, a floppy disk drive, a CD-ROM device, a DVD-ROM device, a DVD-RAM device, a DVD-RW device, a flash memory device, or some other mass storage device known in the art.

System bus 140 represents a shared bus for communicating information and data throughout system 100. System bus 140 represents one or more buses including an industry standard architecture (ISA) bus, a peripheral component interconnect (PCI) bus, a universal serial bus (USB), or some other bus known in the art to provide similar functionality.

Additional components that may be coupled to system 100 through system bus 140 include a display device 150, a keyboard 160, and a cursor control device 170. Display device 150 represents any device equipped to display electronic images and data to a local user or maintainer. Display device 150 is a cathode ray tube (CRT), a liquid crystal display (LCD), or any other similarly equipped display device, screen, or monitor. Keyboard 160 represents an alphanumeric input device coupled to system 100 to communicate information and command selections to processor 110. Cursor control device 170 represents a user input device equipped to communicate positional data as well as command selections to processor 110. Cursor control device 170 includes a mouse, a trackball, a stylus, a pen, cursor direction keys, or other mechanisms to cause movement of a cursor. Network controller 180 links the system 100 to a source of experimental data (not shown).

It should be apparent to one skilled in the art that system 100 may include more or fewer components than those shown in FIG. 1 without departing from the spirit and scope of the present invention. For example, system 100 may include additional memory, such as, for example, a first or second level cache or one or more application specific integrated circuits (ASICs). As noted above, system 100 may be comprised solely of ASICs. In addition, components may be coupled to system 100 including, for example, image scanning devices, digital still or video cameras, or other devices that may or may not be equipped to capture and/or download electronic data to/from system 100.

Figure 2:
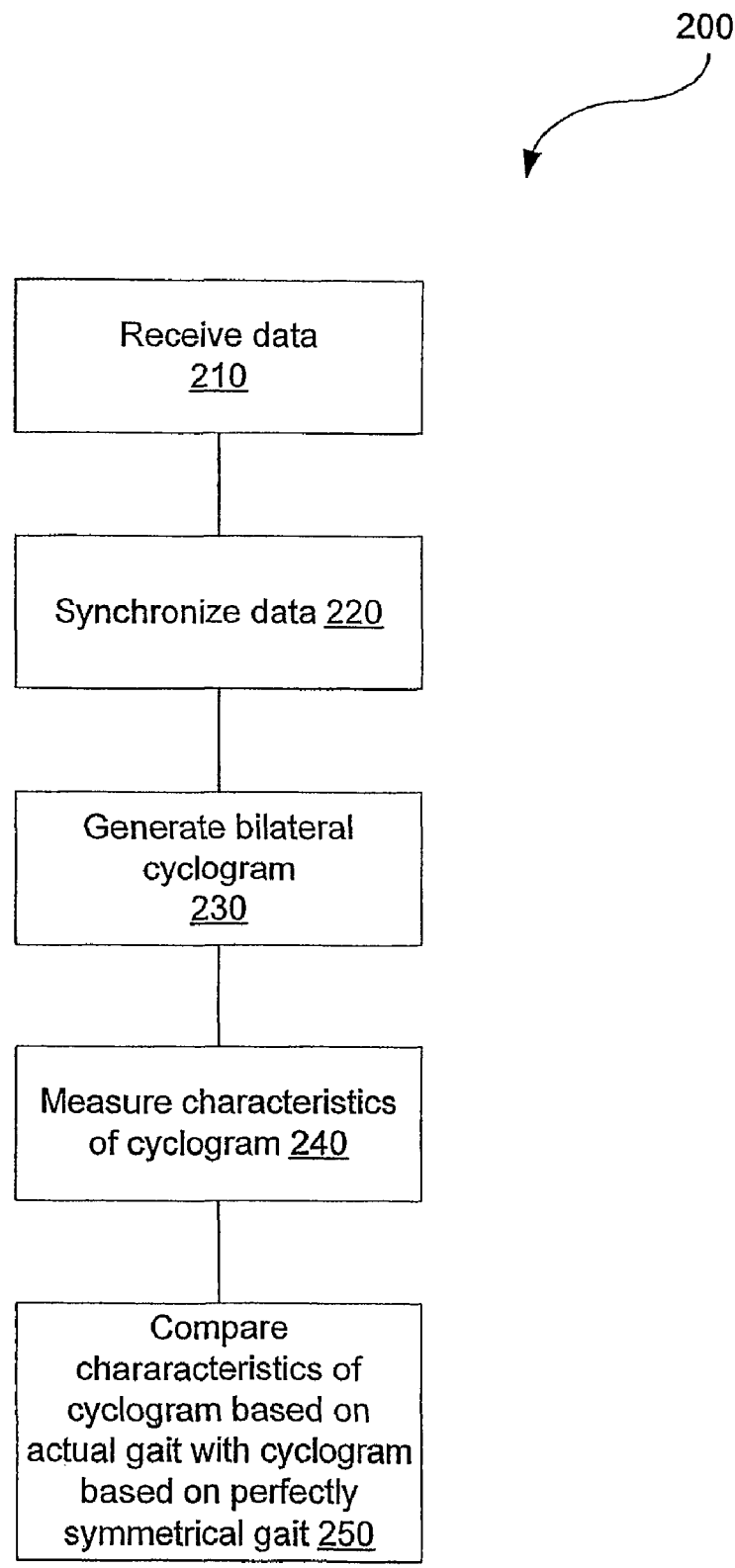
FIG. 2 illustrates a flowchart of a method for quantifying gait asymmetry.

FIG. 2 illustrates a flowchart of a method 200 for quantifying gait asymmetry. First, the system 100 receives 210 experimental data via network controller 180. In one embodiment, the experimental data consists of timestamps and the angles of particular joints at that point in time. The computation of these angles is well known in the art. See, for example, A New Gait Parameterization Technique by Means of Cyclogram Moments: Application to Human Slope Walking, A. Goswami, Gait & Posture 8:15-36 (1998) that is incorporated by reference herein in its entirety. In one embodiment, positions of retro-reflective markers taped on the skin at the extremities of the limb segments (the thigh, the shank, etc.) are recorded while the experimental subject walks. The angles are then computed by assuming the limb segments to be idealized rigid bodies.

Figure 3B:
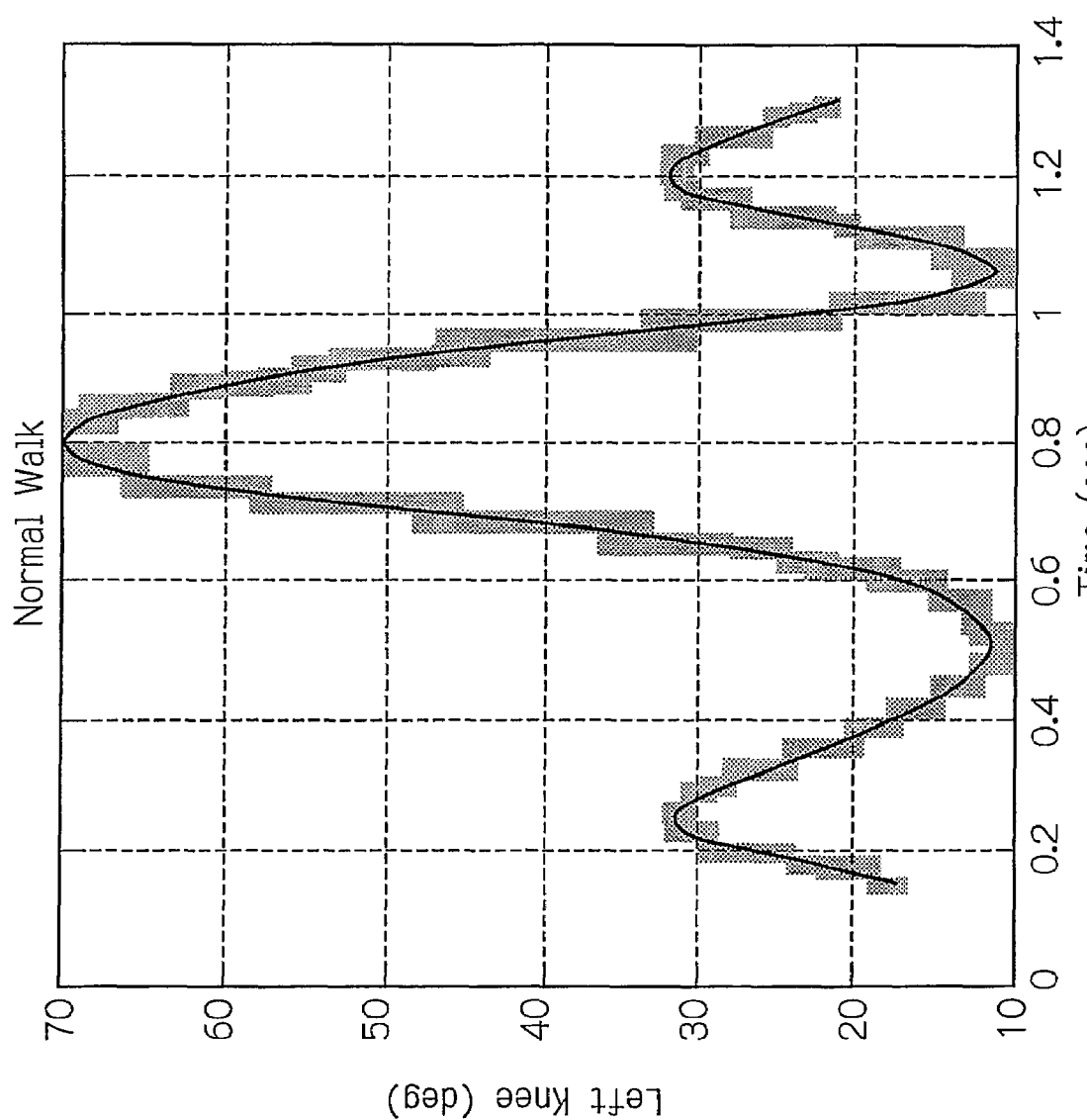
FIG. 3b illustrates a graph of left knee angle versus time, based on the experimental data.
Figure 3C:
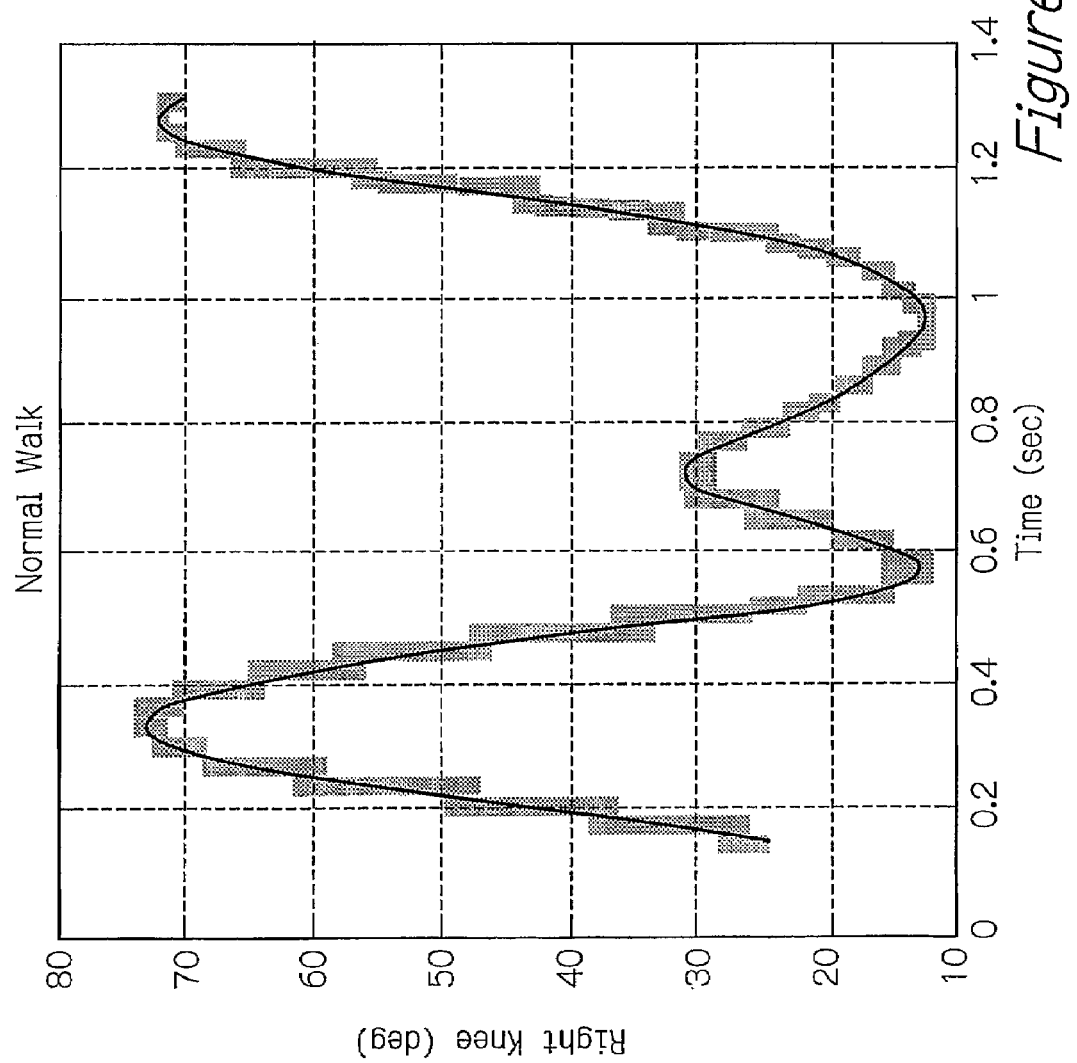
FIG. 3c illustrates a graph of right knee angle versus time, based on the experimental data.

One example of a set of experimental data is given by FIG. 3*a*. Column one contains timestamps. Columns two and three contain angles of the left knee and the right knee, respectively. FIG. 3*b* illustrates a graph of the left knee angle versus time, based on the experimental data. This type of graph is known as a time-angle plot. Note that since walking is a repetitive motion, the cycle (beginning at approximately 0.17 seconds) begins to repeat at approximately 1.17 seconds. Similarly, FIG. 3*c* illustrates a graph of the right knee angle versus time, based on the experimental data.

Figure 3D:
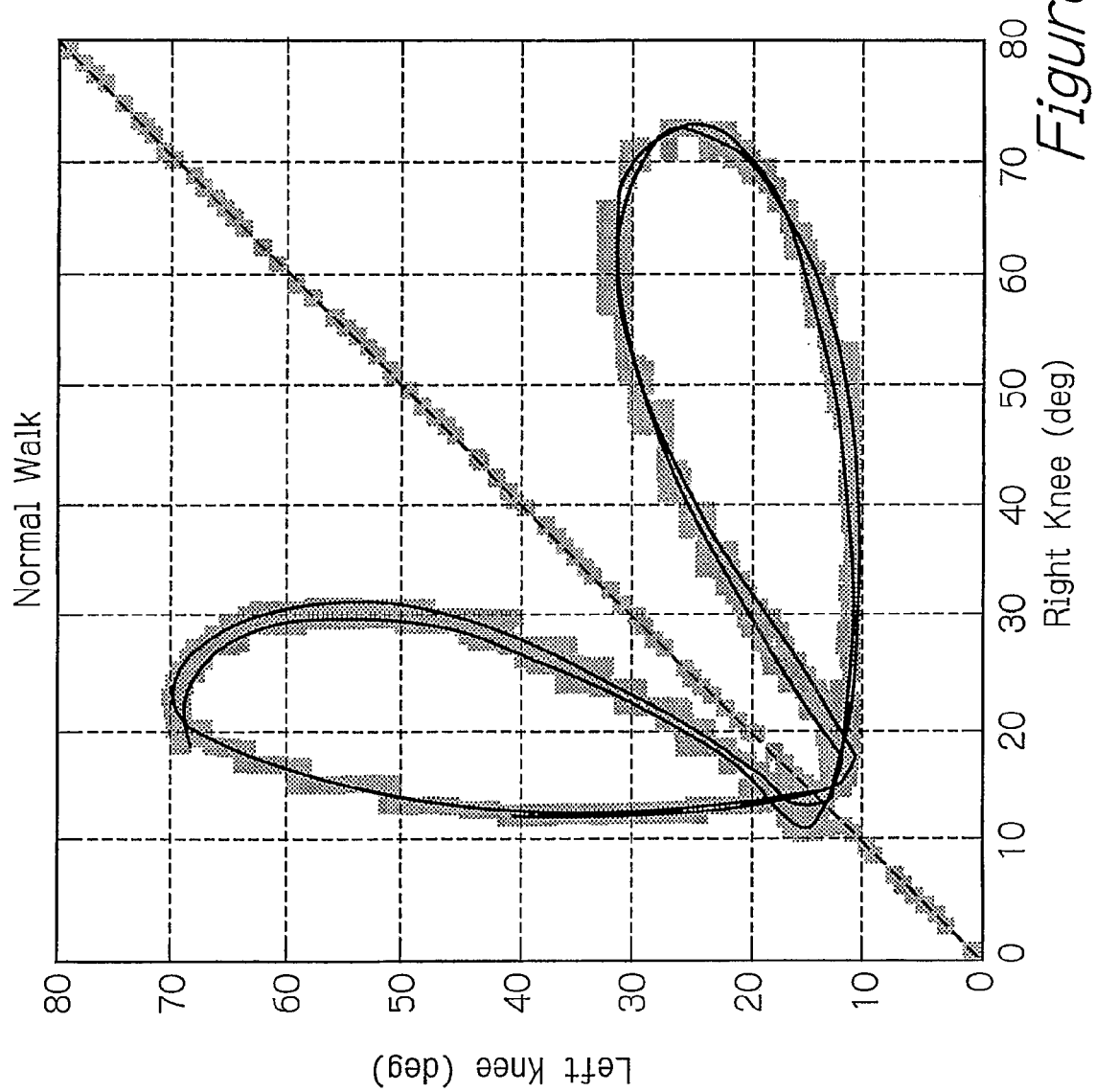
FIG. 3d illustrates a bilateral cyclogram of left knee angle versus right knee angle, based on the experimental data.

FIG. 3*d* illustrates a graph of the left knee angle versus the right knee angle, based on the experimental data. This type of graph is commonly known as a cyclogram (or angle-angle plot). A cyclogram simultaneously plots the angular positions of two joints. It is formed by ignoring the time axis of each curve (e.g., the curves in FIGS. 3*b* and 3*c*) and directly plotting one angle versus another angle. A cyclogram is a type of parametric curve. A parametric curve is obtained by directly plotting the associated variables where each variable is a function of a parameter. In the present context, the joint angles are the associated variables and time is the parameter.

A velocity diagram, which is not yet a standard technique in gait study, likewise plots the angular velocities of two joints. Phase diagrams are very popular in the fields of physics and engineering but not in the field of gait study. In gait study, phase diagrams represent the angular position and angular velocity of the same joint. Our technique is applicable to all of these representations of movements. Phase diagrams, in particular, are interesting since they contain both the position and velocity (i.e., the "state") of a joint. However, since each phase diagram requires two dimensions, a bilateral phase diagram of a single joint will require four dimensions. For phase diagrams, we lose the advantage of direct visualization.

Cyclograms have been used in the past to describe gait. See, for example, A New Gait Parameterization Technique by Means of Cyclogram Moments: Application to Human Slope Walking, A. Goswami, Gait & Posture 8:15-36 (1998). However, until now, these cyclograms have plotted angles of joints that belong to the same limb (for example, the left hip versus the left knee). This invention uses bilateral cyclograms to describe gait. Bilateral cyclograms plot the angle of one joint on one leg versus the angle of the corresponding joint on the other leg. For example, FIG. 3*d* plots the angle of the left knee versus the angle of the right knee.

This discussion focuses on the symmetry of individual leg joints while walking. In order to characterize the overall leg movement symmetry we can study the three principal joints (hip, knee, and ankle) one at a time. The main advantage of this approach is that the cyclograms can be plotted and visualized.

It is entirely possible to mathematically treat multi-joint bilateral cyclograms in the same way single joint cyclograms are treated. For example, we can study a bilateral hip-knee cyclogram in a 4-dimensional space or even a hip-knee-ankle bilateral cyclogram in a 6-dimensional space and compute their deviations from the symmetry line (discussed below).

Because the legs move approximately out-of-phase during normal gait (e.g., see FIGS. 3*b* and 3*c*), the bilateral joint signals cannot be compared directly to test symmetry. In the preferred embodiment, the experimental data is synchronized. Thus, after receiving the experimental data 210, the data is synchronized 220 using synchronization module 121. This synchronization is accomplished by using an identifiable gait event such as the heel touchdown. In other words, the angle data in columns two and three of FIG. 3*a* is realigned so that the angle of the left knee when the left heel touches down corresponds to the angle of the right knee when the right heel touches down.

Figure 3E:
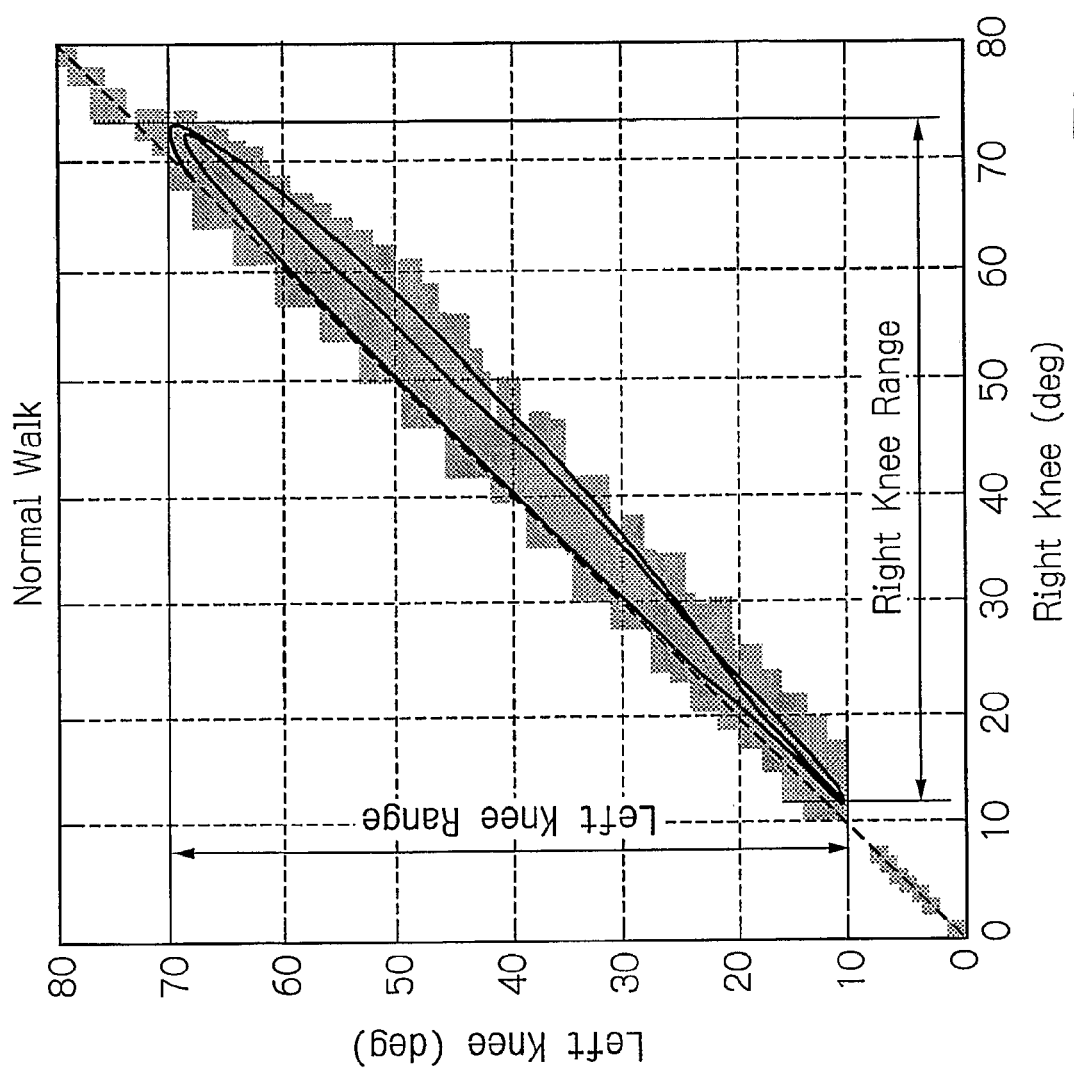
FIG. 3e illustrates a bilateral cyclogram of left knee angle versus right knee angle, based on the experimental data, where the angle data has been synchronized.
Figure 4A:
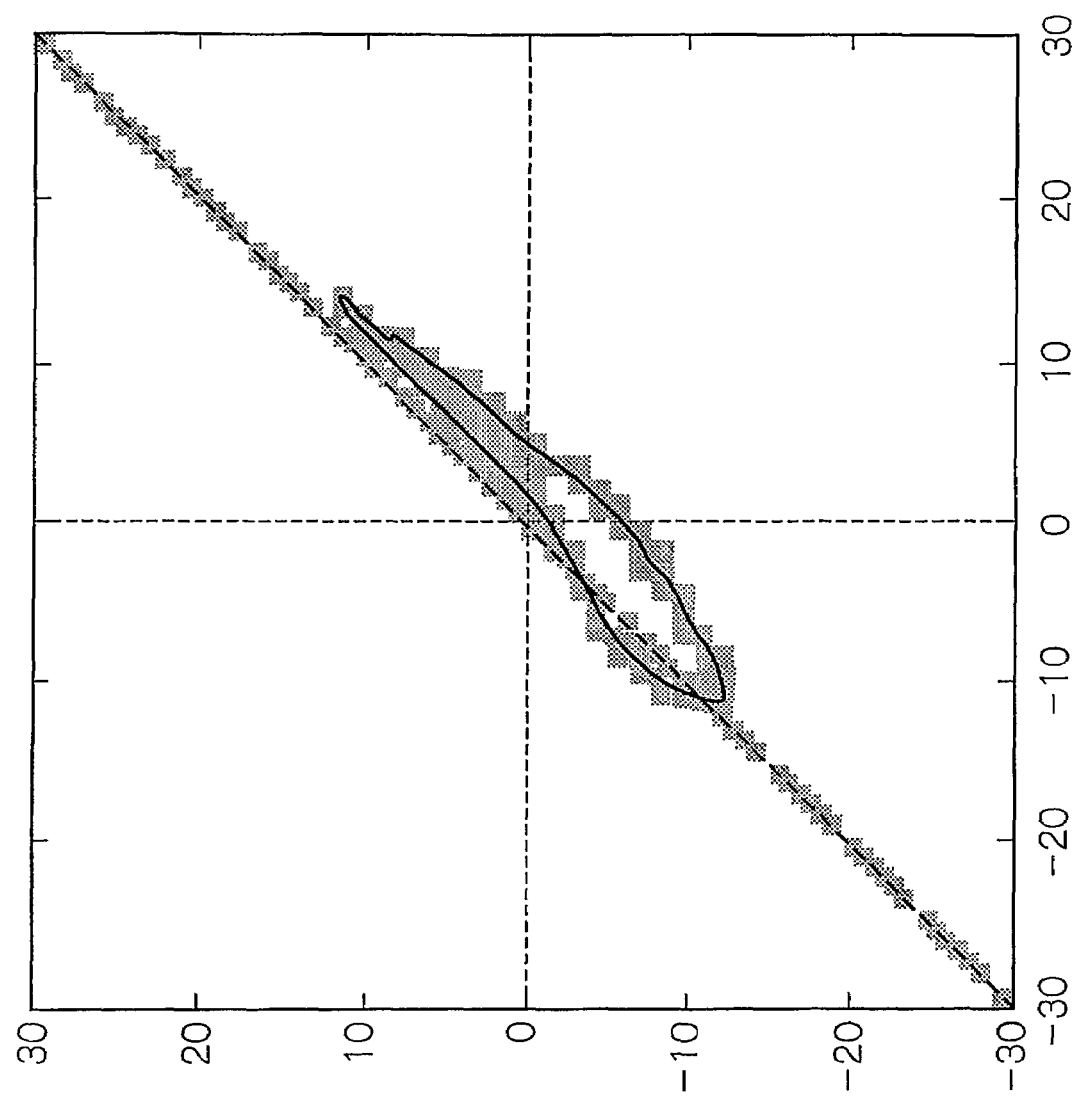
Figure 4B:
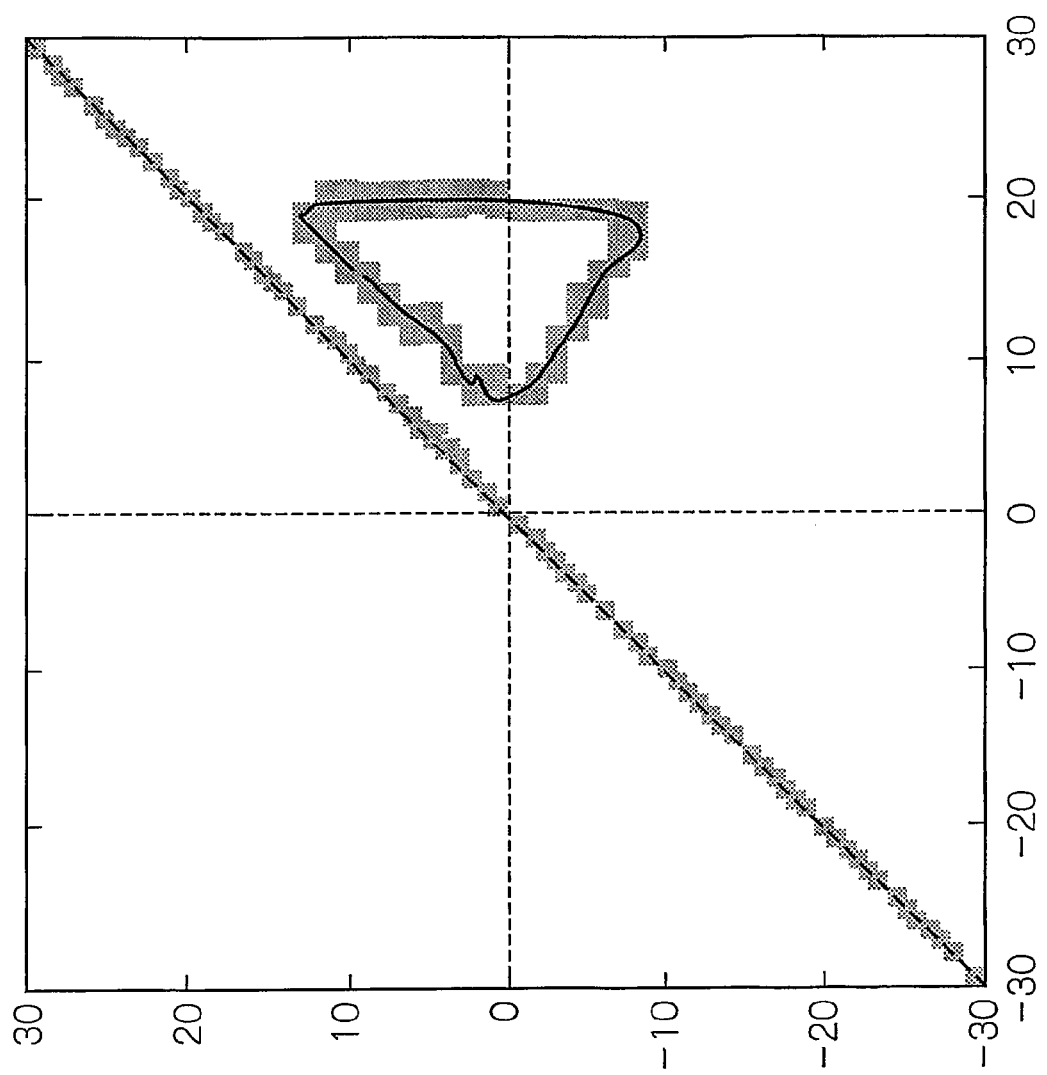
Figure 4C:
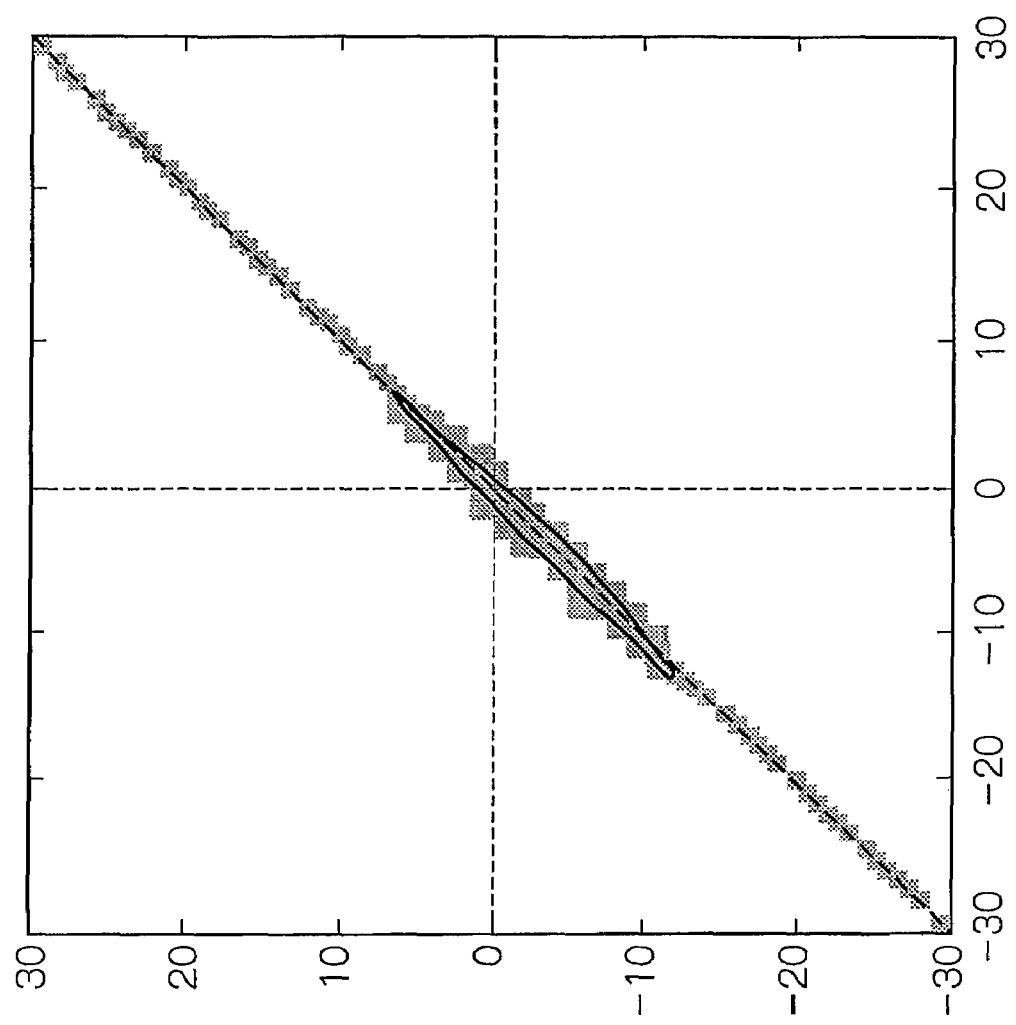
Figure 4D:
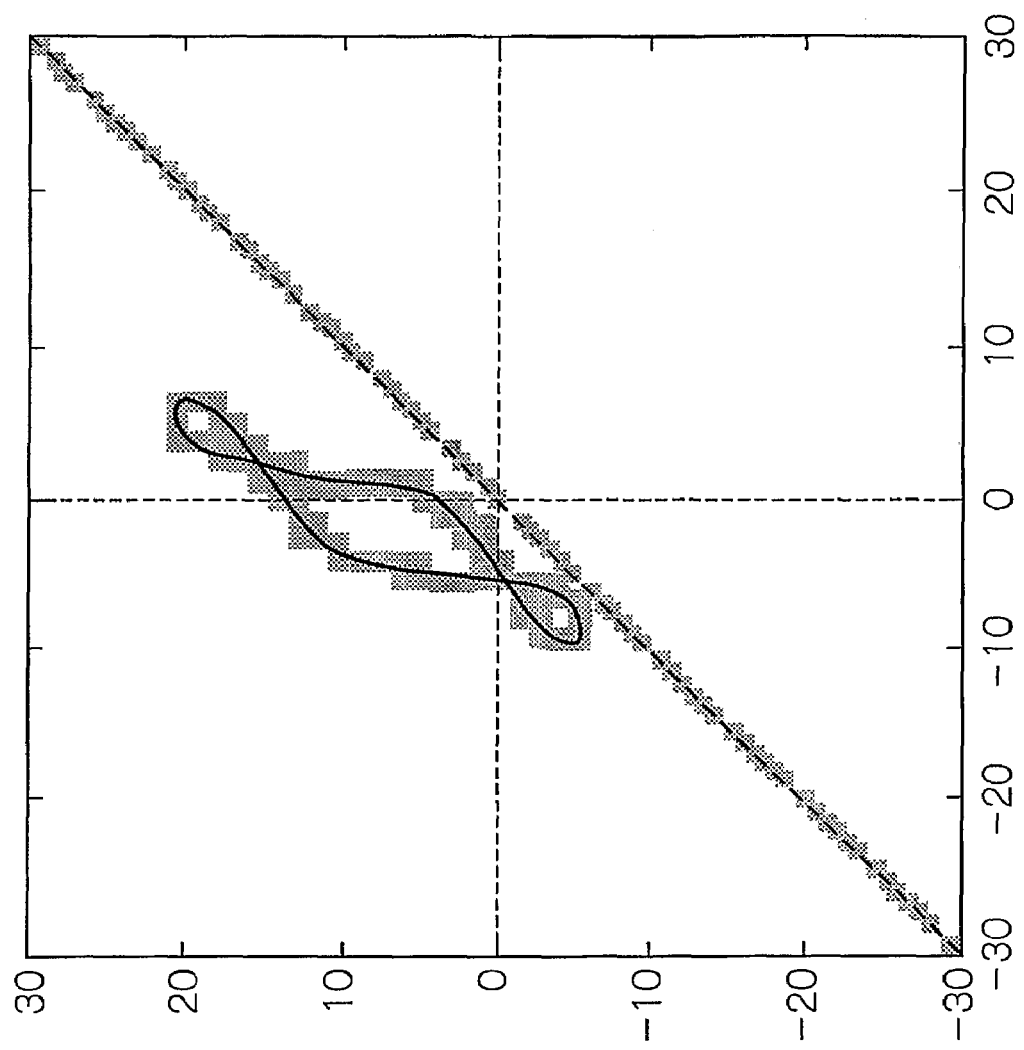
Figure 4E:
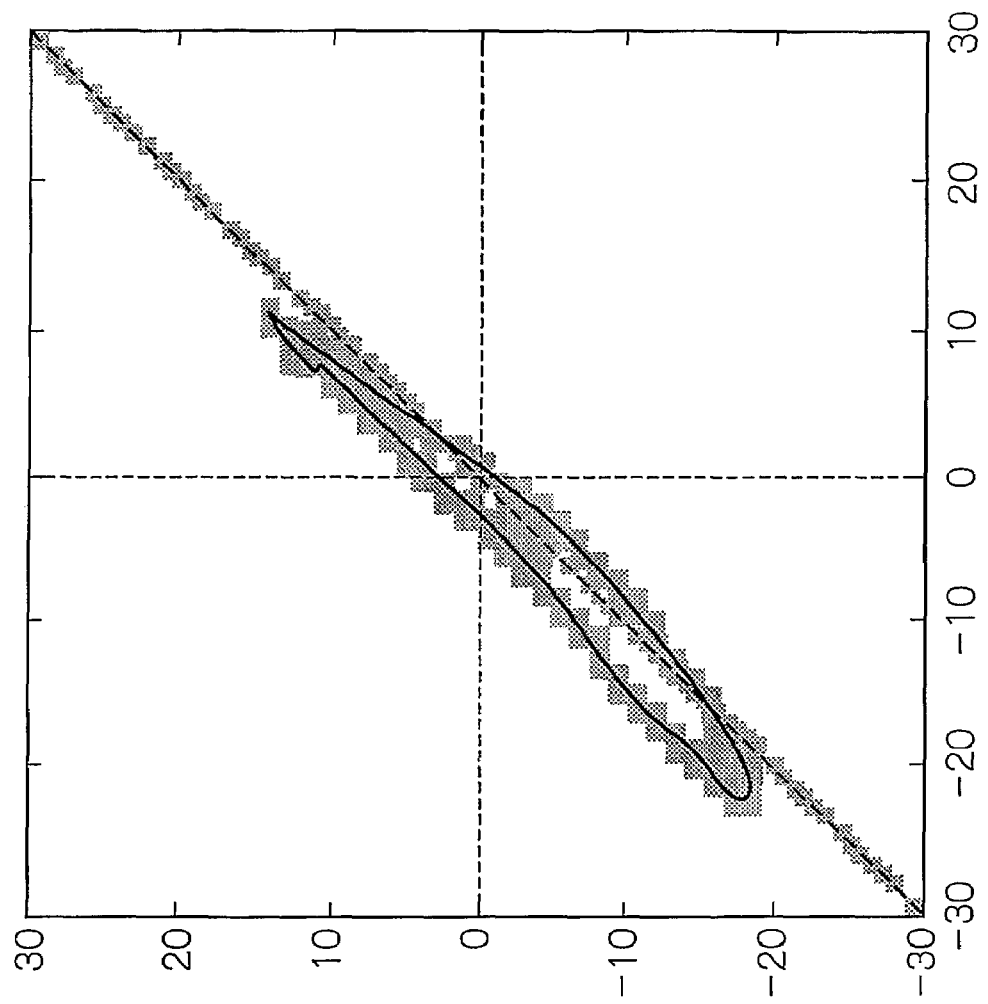
Figure 4F:
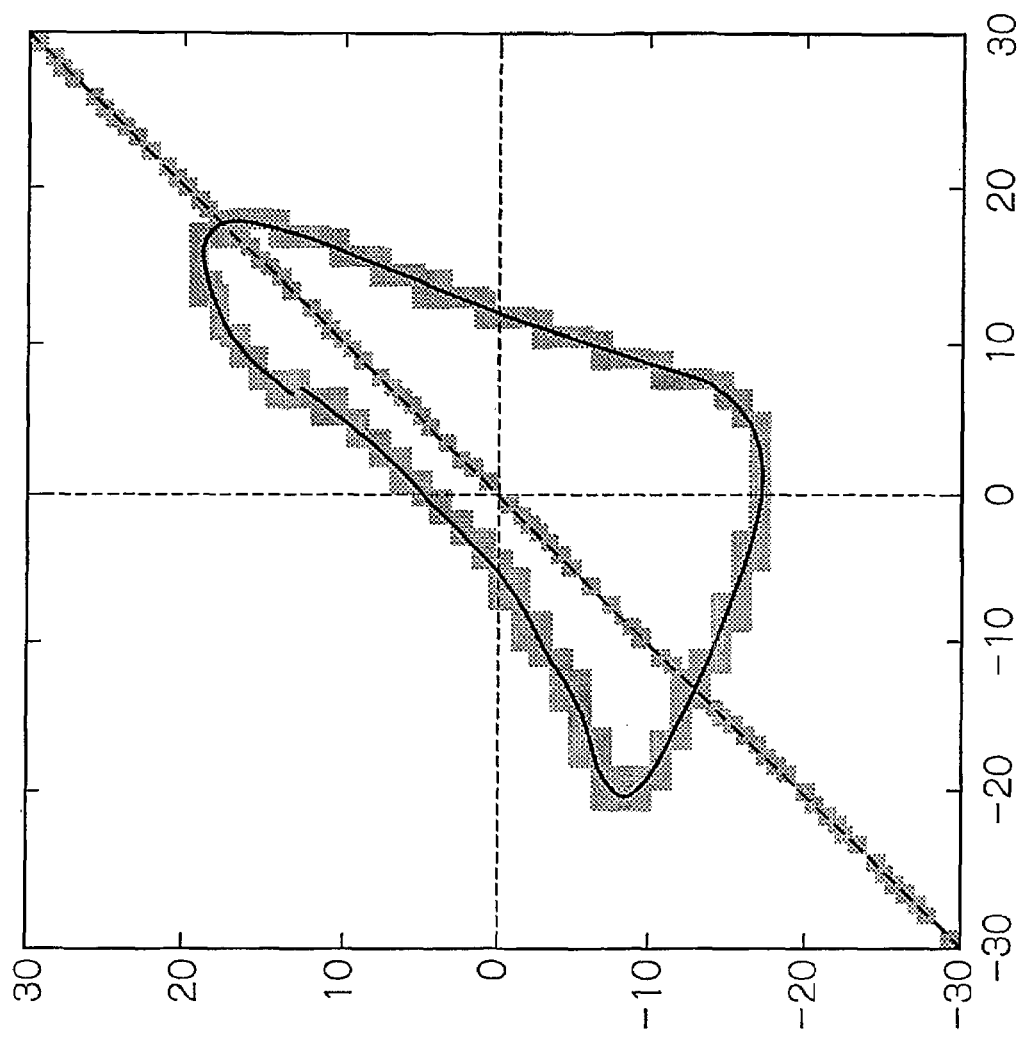
Figure 4G:
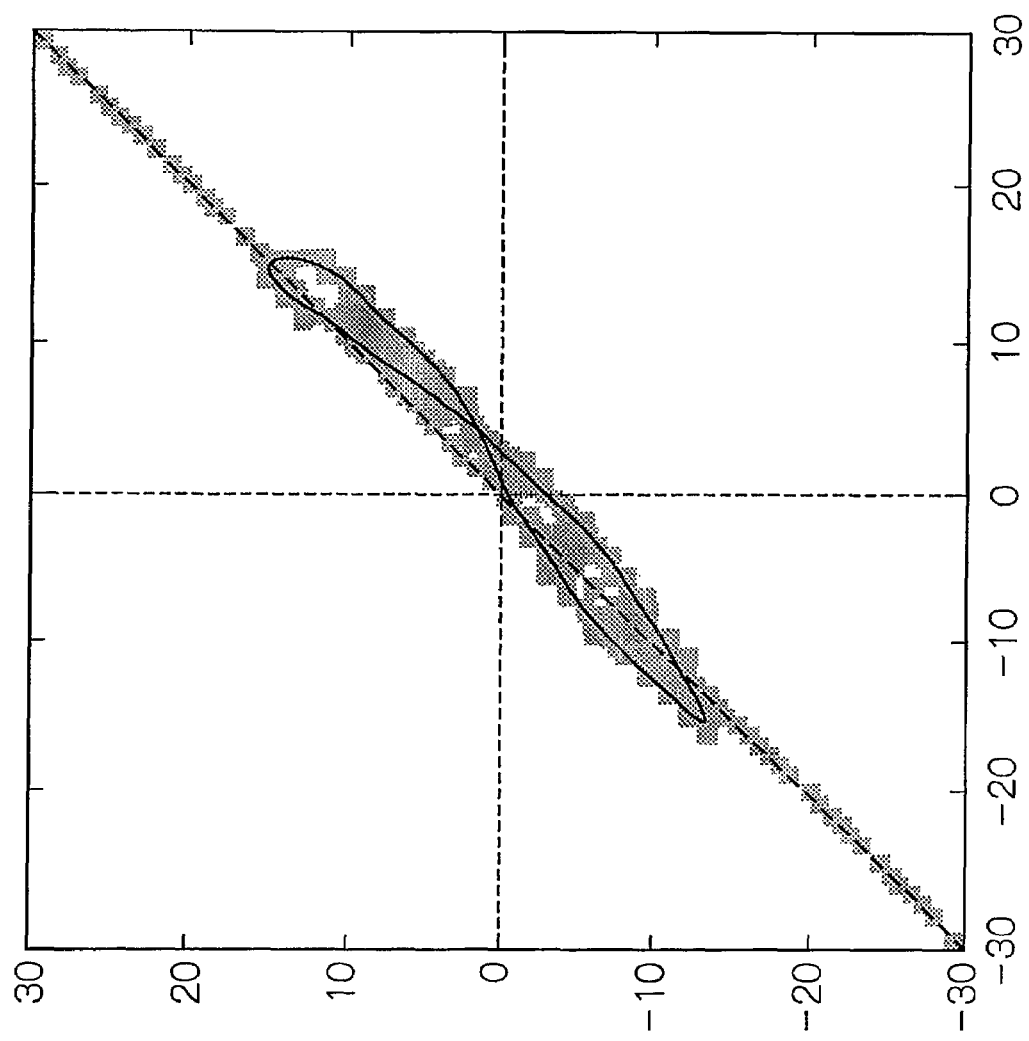
Figure 4H:
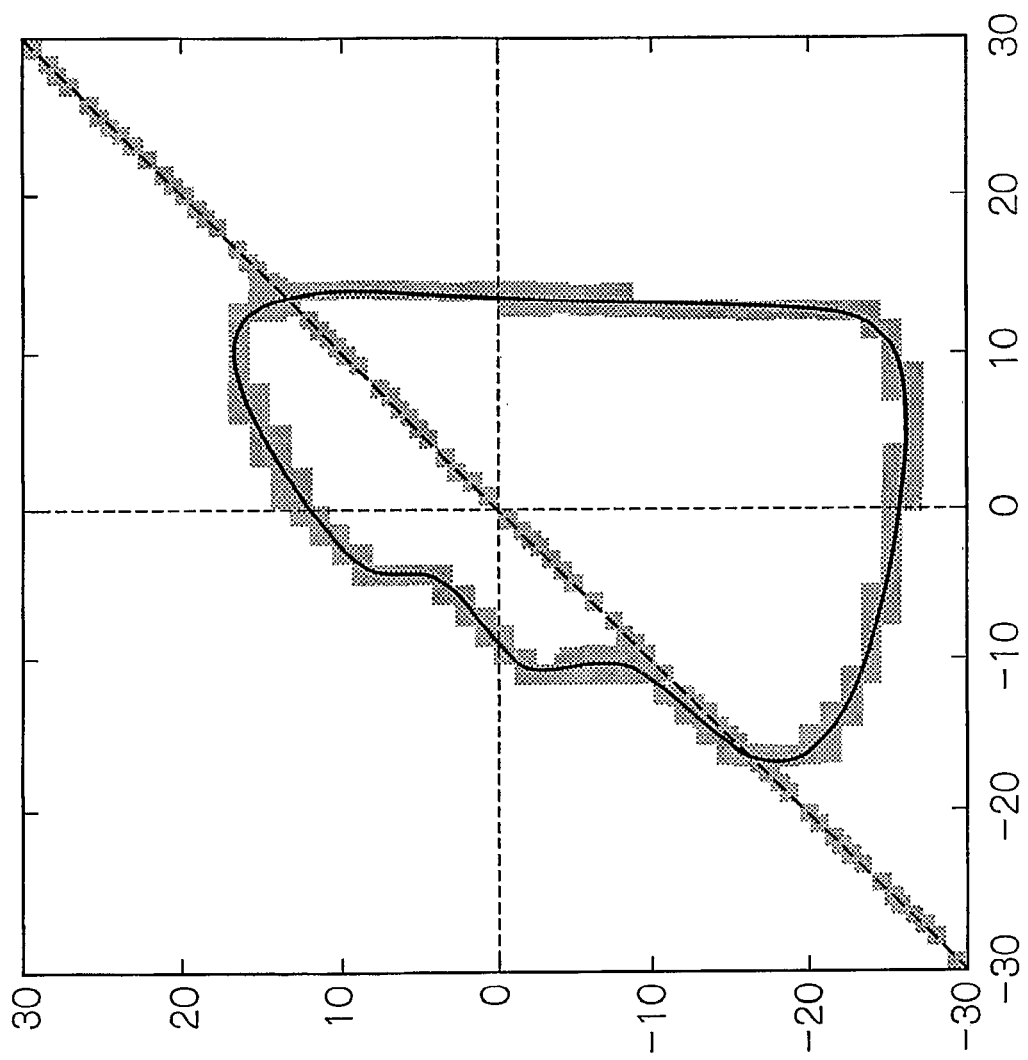
Figure 4I:
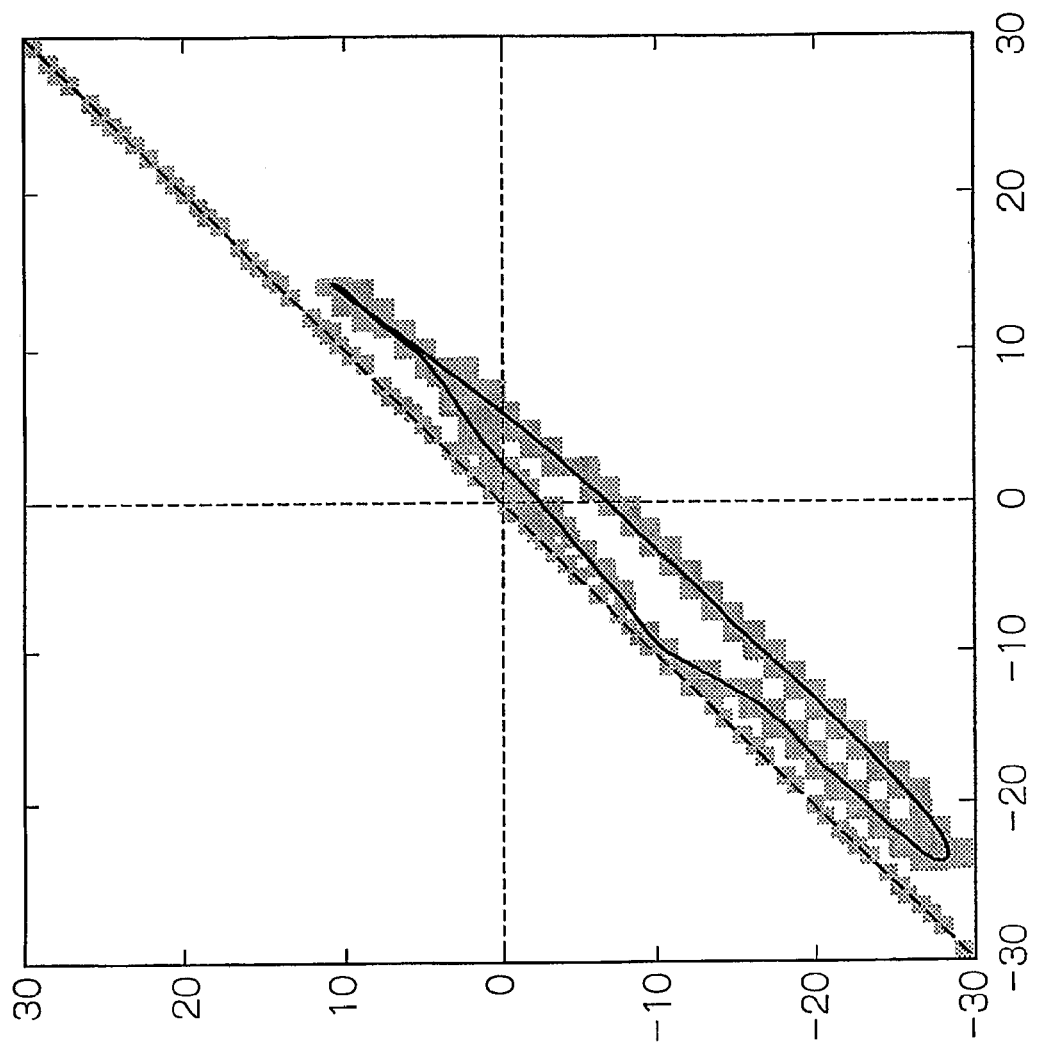
Figure 4J:
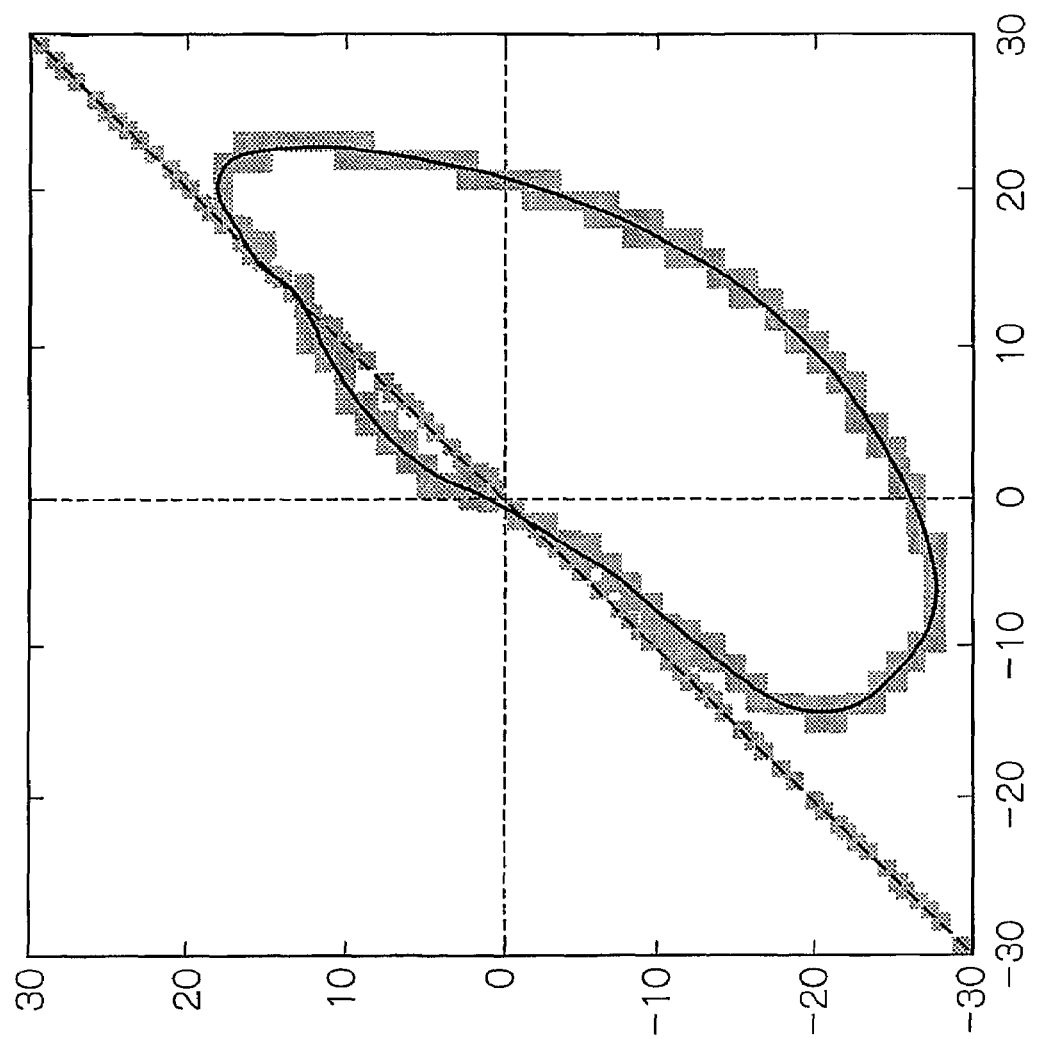
Figure 4K:
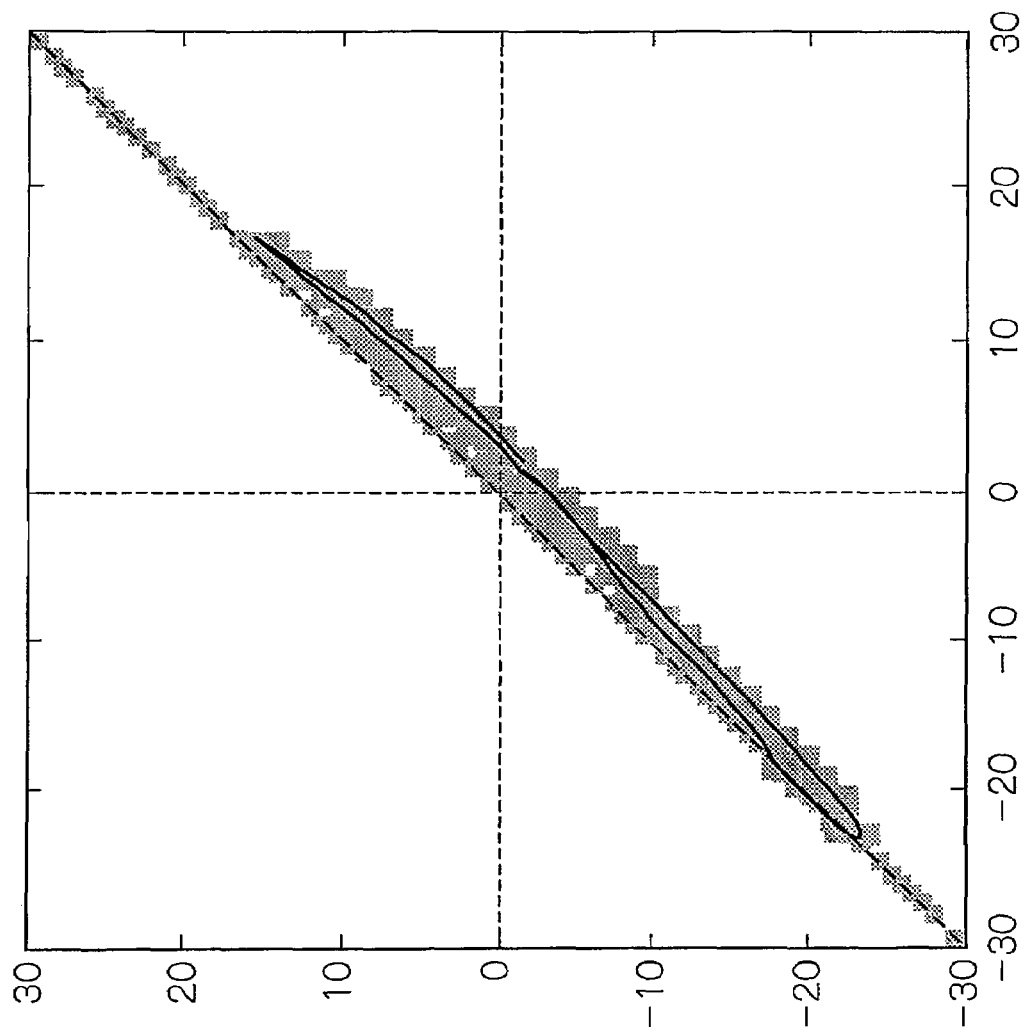
Figure 41:
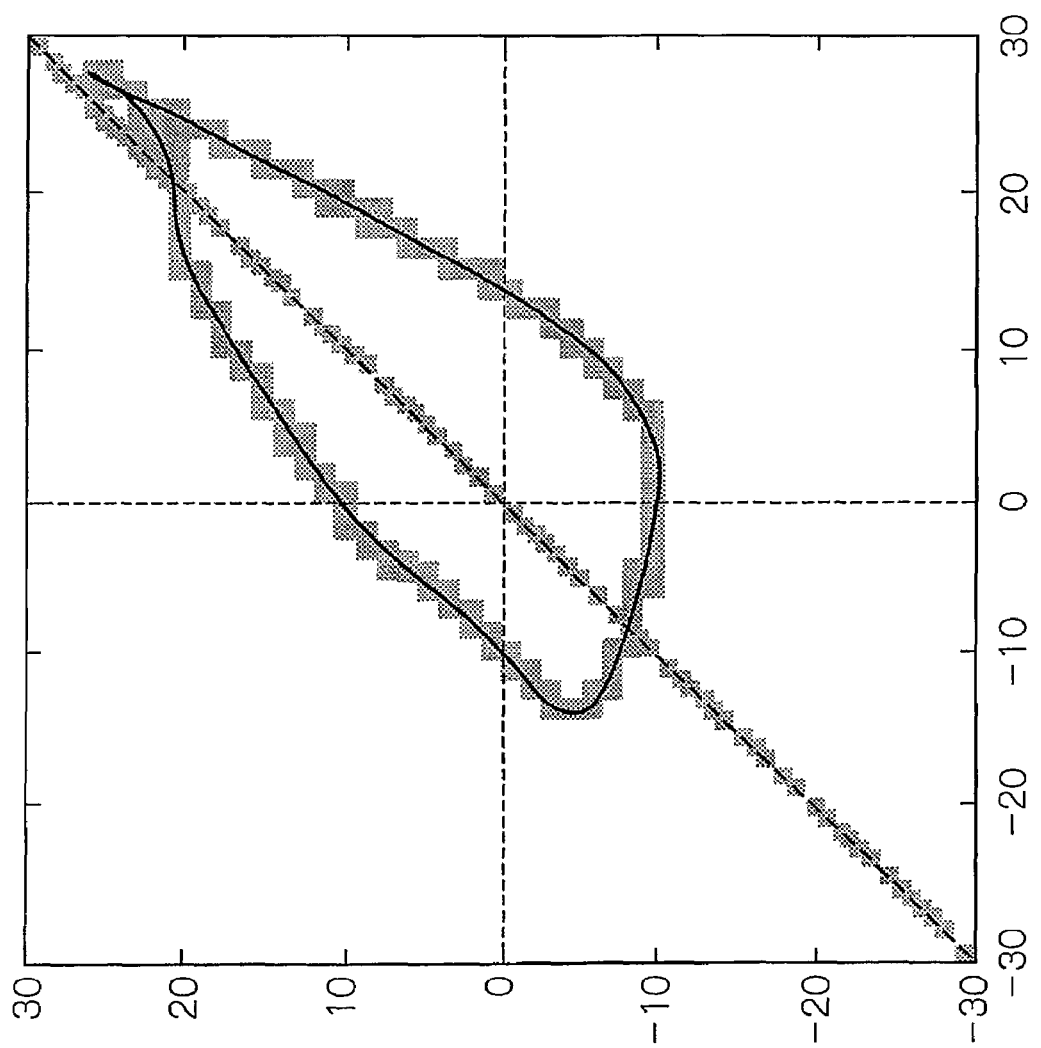

In one embodiment, the synchronized data is then used to generate a (bilateral) cyclogram 230. FIG. 3*e* illustrates this cyclogram, which is based on synchronized experimental data. A cyclogram can be described using certain characteristics or parameters. In one embodiment, these characteristics include the area within the cyclogram, the orientation of the cyclogram, and the minimum moment of the cyclogram. Other potential candidate parameters include: a) the distance of the "center of mass" of the cyclogram from the symmetry line (ideally, it should be zero); b) the maximum moment of the cyclogram (ideally, it should be infinity); c) the "circularity" of the cyclogram (ideally, it should be zero); d) other moments of the cyclogram (for each cyclogram, there exists an infinite series consisting of moments of progressively higher orders; the minimum moment mentioned above is a second-order moment and is a part of this series; some of the other lower order components may be useful); e) the Fourier Descriptors of the cyclograms (one can compute the Fourier Descriptors of the cyclograms and distinguish them from the symmetry line; there is an infinite series of Fourier Descriptors, and the lower order components can be useful); and f) virtually any image processing technique employed to detect, distinguish, and classify shapes. Additional details regarding cyclogram characteristics and parameters are found in A New Gait Parameterization Technique by Means of Cyclogram Moments: Application to Human Slope Walking, A. Goswami, Gait & Posture 8:15-36 (1998).

A synchronized bilateral cyclogram generated based on a perfectly symmetrical gait is a line having a slope of 1 that crosses through the origin (0,0). This is because the joint angle on the left leg behaves identically to the corresponding joint angle on the right leg once the data has been synchronized. The characteristics of such a synchronized bilateral cyclogram are as follows: the area within it is zero; its orientation is 45°; and its minimum moment is zero.

In one embodiment, after generating the (synchronized) bilateral cyclogram 230, the characteristics of the cyclogram are measured 240 using characteristic computation module 122. In another embodiment, the characteristics of the cyclogram are measured directly from the synchronized data without actually generating the cyclogram. These characteristics are then compared 250 with those of a cyclogram generated from a perfectly symmetrical gait or some other baseline. By measuring the deviation of a generated cyclogram from the "ideal" cyclogram, the characteristics are able to quantify the asymmetry of the actual gait (i.e., the deviation of the actual gait from the perfectly symmetrical or baseline gait).

As illustrated in FIG. 3e, the area within the cyclogram is greater than zero, its orientation is less than 45°, and its minimum moment is greater than zero. These three characteristics help quantify the asymmetry of the actual gait. In one embodiment, normalized units are used to express cyclogram characteristics. In another embodiment, the units are normalized based on statistical averages of data from many experimental subjects.

FIGS. 4a-l illustrate synchronized bilateral hip cyclograms of two sets of experimental subjects: "normal" subjects and subjects with gait pathologies. FIGS. 4a, 4c, 4e, 4g, 4i, and 4k concern normal subjects (experimental subjects #1, 3, etc.), while FIGS. 4b, 4d, 4f, 4h, 4j, and 4l concern subjects with gait pathologies (experimental subjects #2, 4, etc.). In this embodiment, the gait pathologies are caused by strokes.

Figure 5A:
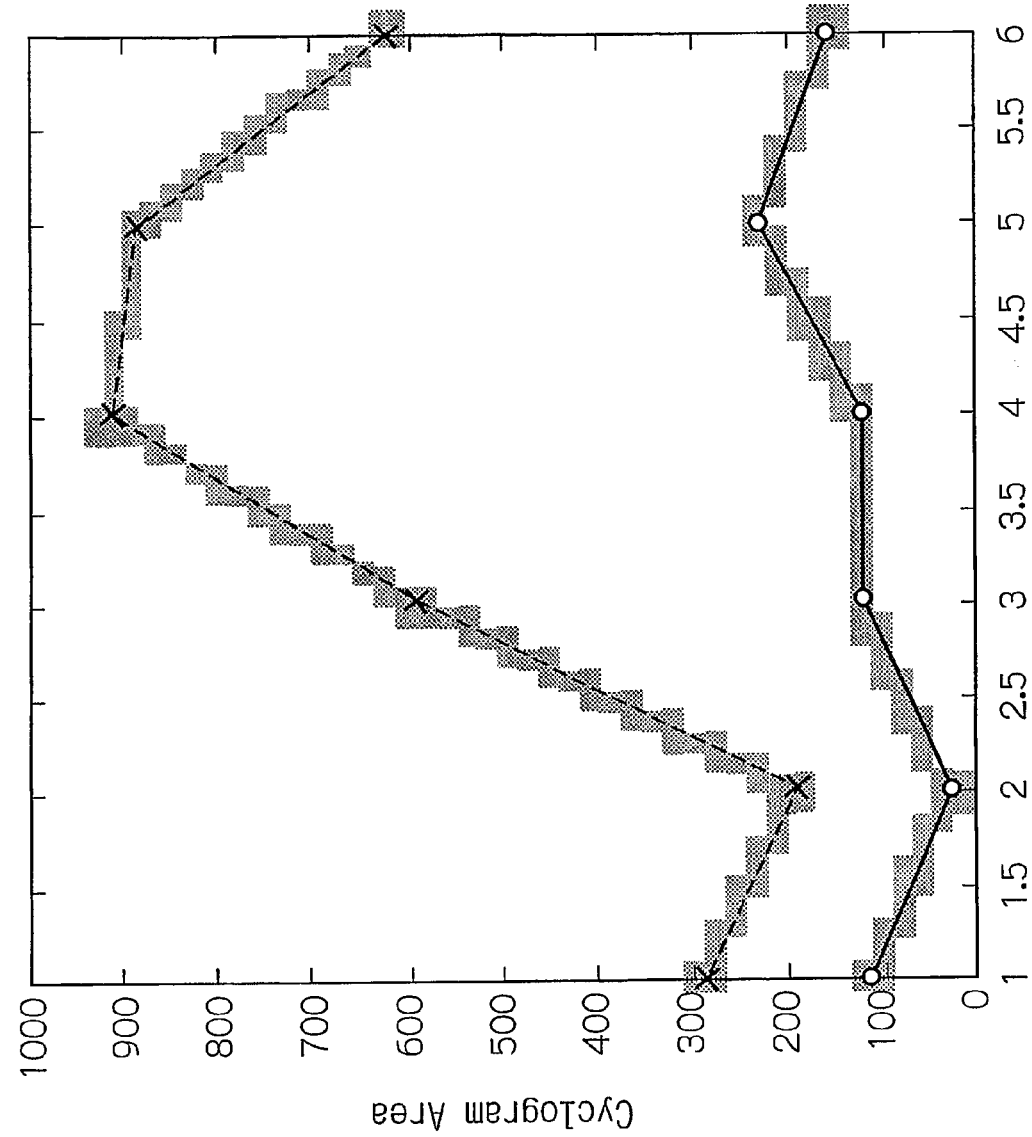
FIG. 5a illustrates a graph of the areas of the synchronized bilateral hip cyclograms in FIGS. 4a-l.
Figure 5C:
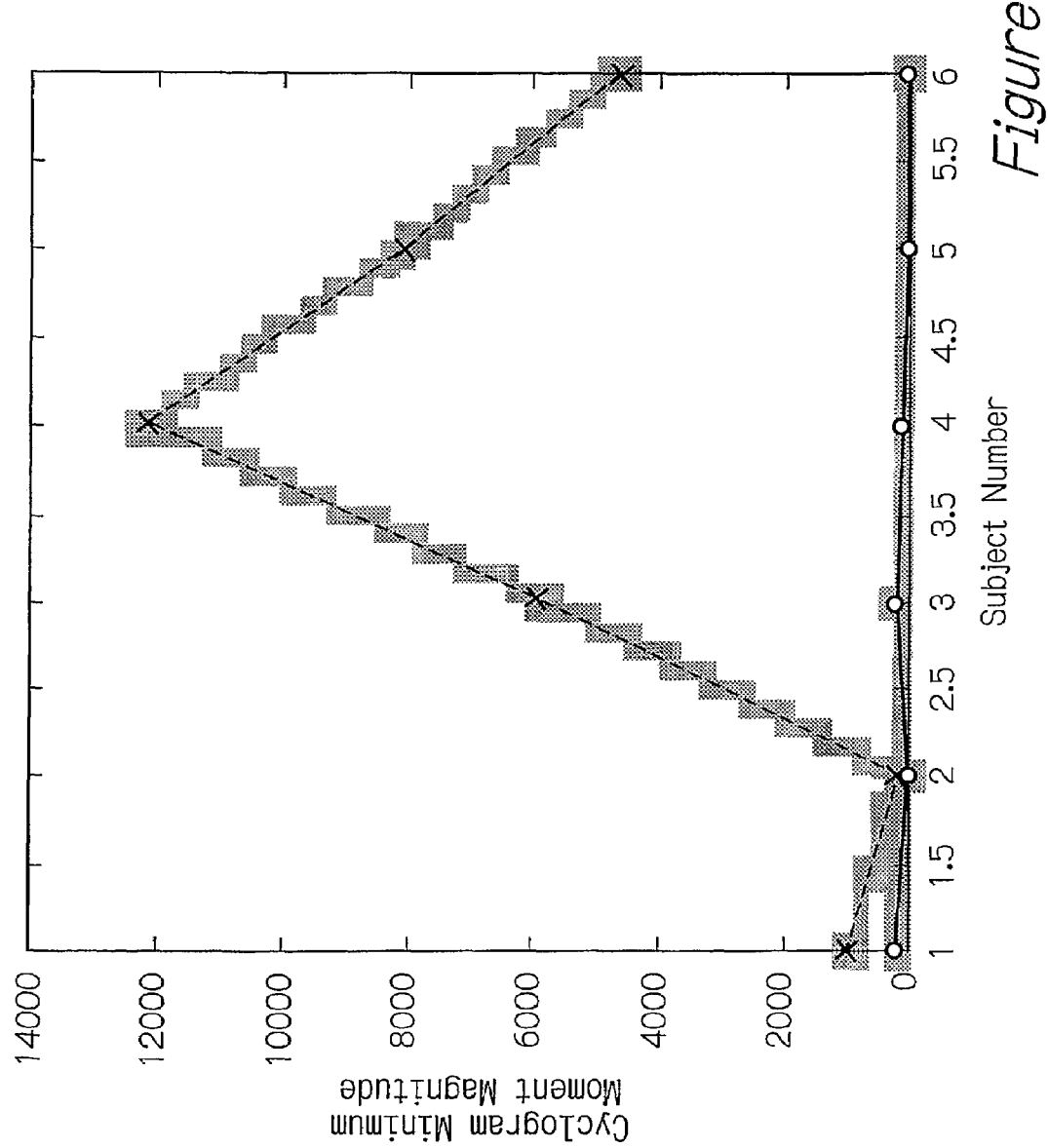
FIG. 5c illustrates a graph of the minimum moment magnitudes of the synchronized bilateral hip cyclograms in FIGS. 4a-l.

FIGS. 5a-c illustrate graphs of particular characteristics of the synchronized bilateral hip cyclograms in FIGS. 4a-l. The "X"s represent subjects with gait pathologies, while the dots represent normal subjects. FIG. 5a illustrates a graph of the area of the cyclogram for each experimental subject. As mentioned above, the synchronized bilateral cyclogram of a perfectly symmetrical gait has an area of zero. FIG. 5a shows that while the group of normal subjects had cyclograms with areas greater than zero, the areas were significantly smaller than those of the group of subjects with gait pathologies.

FIG. 5b illustrates a graph of the orientation of the cyclogram for each experimental subject. As mentioned above, the synchronized bilateral cyclogram of a perfectly symmetrical gait has an orientation of 45°. FIG. 5b shows that while the group of normal subjects had cyclograms with orientations at or close to 45°, the group of subjects with gait pathologies had many cyclograms with orientations nowhere near 45°.

FIG. 5c illustrates a graph of the minimum moment magnitude of the cyclogram for each experimental subject. As mentioned above, the synchronized bilateral cyclogram of a perfectly symmetrical gait has minimum moment magnitude of zero. FIG. 5c shows that while the group of normal subjects had cyclograms with minimum moment magnitudes very close to zero, the group of subjects with gait pathologies had many cyclograms with minimum moment magnitudes much larger than zero.

Figure 6:
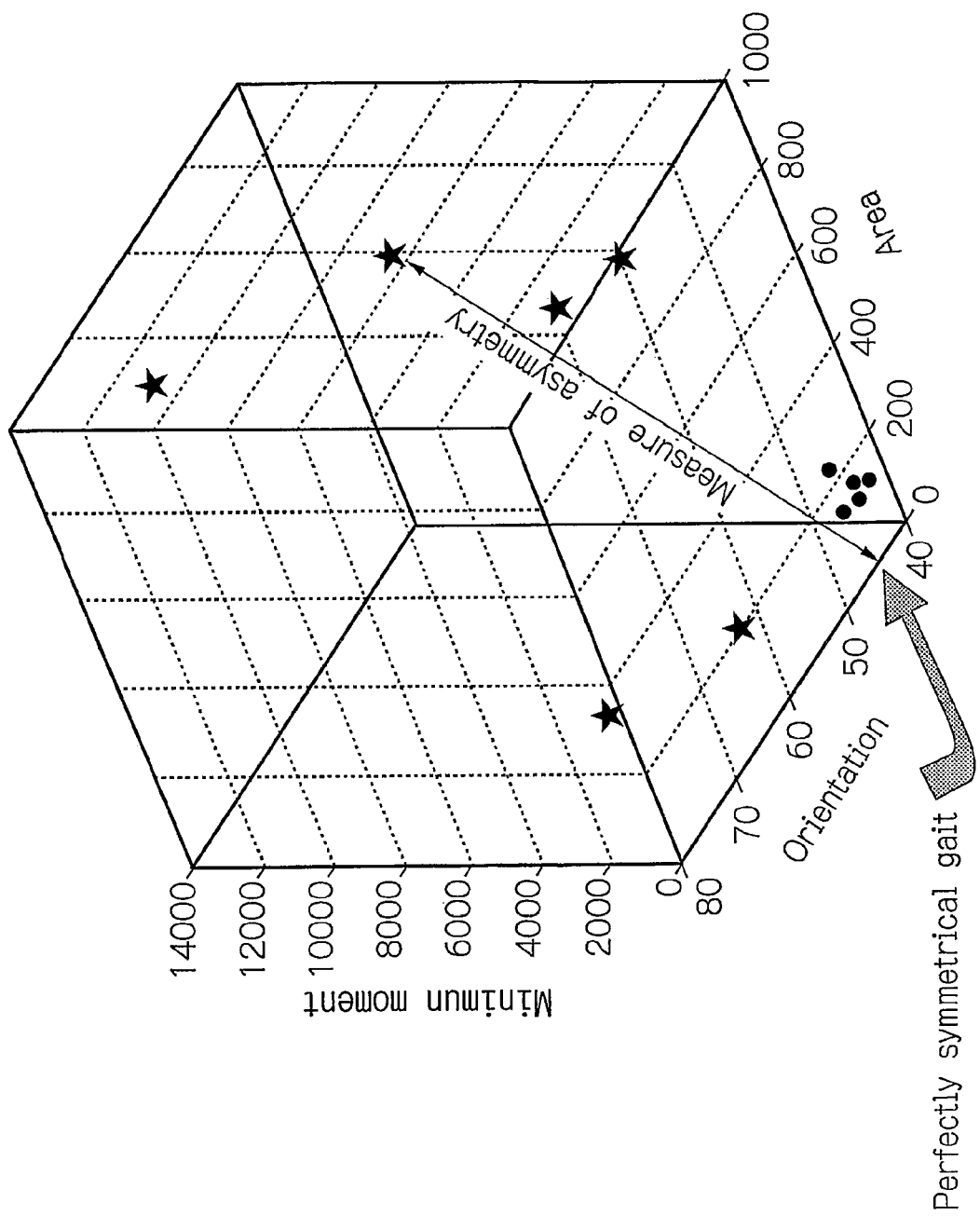
FIG. 6 illustrates a three-dimensional plot of the information contained in FIGS. 5a, 5b, and 5c.

FIG. 6 illustrates a three-dimensional plot of the information contained in FIGS. 5a, 5b, and 5c. Each of the three axes represents a different characteristic of a cyclogram: area, orientation, and minimum moment magnitude. The locations of synchronized bilateral cyclograms based on pathological gaits are shown by stars, while the locations of cyclograms based on normal gaits are shown by dots. The location of a cyclogram formed from a perfectly symmetrical gait is shown by a diamond shape and is located at <0, 45, 0>. As shown in FIG. 6, the normal gaits are located close to the perfectly symmetrical gait, while the pathological gaits are not.

As long as one uses three (any three) or fewer characteristics to describe a cyclogram, the results can be visualized. Although a "measure of asymmetry," similar to that shown in FIG. 6, can be mathematically computed in a higher-dimensional space—thereby allowing the use of more parameters—we lose the advantage of visualization.

The application field of the symmetry quantification technique presented above is not restricted to gait study or even to human movements. In fact, the technique can be applied without modification to any movement where symmetry is expected—both in machines (such as humanoid robots) and in biological entities (humans, cats, cockroaches, etc.). The above example focused on gait, but the technique can, also quantify symmetry in human arm movements, leg movements of quadruped animals, and, with proper adaptation, wing movement of birds or insects and fin movement of fishes and other aquatic creatures. This is accomplished because the method is based on the comparison of numerical kinematic (position) data of the two movements under study, usually from the left and right sides of the body, end does not depend on or make use of any assumption regarding the particular type of movement.

Also note that the implication of symmetry is one of similarity between two movements. Therefore, by extension, one may employ the technique to measure the similarity of movements between two persons. One can, for example, measure the left arm movement of one person to the left arm movement of another person. This also applies to all of the other examples mentioned above.

The discussion above was based on joint movements represented by angular quantities. This was a specific situation given the context of gait study. Joint motion is not a prerequisite for the applicability of this method. In other words, instead of quantifying the knee joint movement symmetry, we could equally quantify the symmetry in the knee position or the position of the tip of the big toe. Note however, that the term cyclogram is associated with joint motion. So, we are not restricted to using the traditional joint-level cyclograms for employing this technique.

Cyclic or repetitive movements are particularly suitable to this technique since the corresponding cyclograms are compact curves. However, the general spirit of this technique, which is to measure the deviation from the symmetry line, is also applicable to non-cyclic movements. Some of the suggested parameters, such as the enclosed area, will not be relevant, but others, such as orientation and moments, remain meaningful.

Although the invention has been described in considerable detail with reference to certain embodiments thereof, other embodiments are possible as will be understood to those skilled in the art.

What is claimed is:

1. A method for quantifying asymmetry of joint angles of two limbs during a movement, comprising:
    determining a first set of data that comprises angles of a joint of a first limb as the first limb performs the movement;
    determining a second set of data that comprises angles of a joint of a second limb as the second limb performs a similar movement, wherein the two limbs comprise the first limb and the second limb;
    determining a plurality of data pairs, wherein each data pair includes a first angle from the first set of data and a second angle from the second set of data, and wherein the first angle occurs when the first limb performs an indentifiable event during the movement, and wherein the second angle occurs when the second limb performs the identifiable event during the movement;
    generating a cyclogram in two-dimensional space based on the determined plurality of data pairs by treating each data pair as a point; and
    determining a value of a characteristic of the generated cyclogram, wherein the value quantifies asymmetry of joint angles of the first limb and the second limb.

2. The method of claim 1 wherein the first limb is part of a first body and wherein the second limb is part of the first body.

3. The method of claim 1 wherein the first limb is part of a first body and wherein the second limb is part of a second body.

4. The method of claim 1 wherein the first limb comprises a leg.

5. The method of claim 1 wherein the first limb comprises an arm.

6. The method of claim 1 wherein the movement comprises one or more cycles.

7. The method of claim 1 wherein the characteristic of the generated cyclogram comprises an area of the generated cyclogram.

8. The method of claim 1 wherein the characteristic of the generated cyclogram comprises an orientation of the generated cyclogram.

9. The method of claim 1 wherein the characteristic of the generated cyclogram comprises a minimum moment magnitude of the generated cyclogram.

10. The method of claim 1 farther comprising comparing the determined value to a value of the characteristic of a cyclogram representing a baseline movement.

11. The method of claim 10 wherein the baseline movement comprises a perfectly symmetrical movement.

12. A system for quantifying asymmetry of joint angles of two limbs during a movement, comprising:
    a first determination module configured to determine a first set of data that comprises angles of a joint of a first limb as the first limb performs the movement;
    a second determination module configured to determine a second set of data that comprises angles of a joint of a second limb as the second limb performs a similar movement, wherein the two limbs comprise the first limb and the second limb;
    a data pair module configured to determine a plurality of data pairs, wherein each data pair includes a first angle from the first set of data and a second angle from the second set of data, and wherein the first angle occurs when the first limb performs an indentifiable event during the movement, and wherein the second angle occurs when the second limb performs the identifiable event during the movement;
    a generation module configured to generate a cyclogram in two-dimensional space based on the determined plurality of data pairs by treating each data pair as a point; and
    a third determination module configured to determine a value of a characteristic of the generated cyclogram, wherein the value quantifies asymmetry of joint angles of the first limb and the second limb.

13. A computer program product for quantifying asymmetry of joint angles of two limbs during a movement, including a computer readable medium, which comprises instructions to perform the following:
    determining a first set of data that comprises angles of a joint of a first limb as the first limb performs the movement;
    determining a second set of data that comprises angles of a joint of a second limb as the second limb performs a similar movement, wherein the two limbs comprise the first limb and the second limb;
    determining a plurality of data pairs, wherein each data pair includes a first angle from the first set of data and a second angle from the second set of data, and wherein the first angle occurs when the first limb performs an indentifiable event during the movement, and wherein the second angle occurs when the second limb performs the identifiable event during the movement;
    generating a cyclogram in two-dimensional space based on the determined plurality of data pairs by treating each data pair as a point; and
    determining a value of a characteristic of the generated cyclogram, wherein the value quantifies asymmetry of joint angles of the first limb and the second limb.

14. The method of claim 1 wherein the joint of the second limb corresponds to the joint of the first limb.

15. The method of claim 1 wherein the plurality of data pairs represents the first limb and the second limb performing their movements in phase.

16. The method of claim 1 wherein the identifiable event comprises a gait event.

17. The method of claim 1 wherein the identifiable event comprises a heel touchdown.

* * * * *

UNITED STATES PATENT AND TRADEMARK OFFICE
CERTIFICATE OF CORRECTION

| | | |
|---|---|---|
| PATENT NO. | : 7,503,900 B2 | Page 1 of 1 |
| APPLICATION NO. | : 10/613116 | |
| DATED | : March 17, 2009 | |
| INVENTOR(S) | : Ambarish Goswami | |

It is certified that error appears in the above-identified patent and that said Letters Patent is hereby corrected as shown below:

Column 7, line 19, delete "indentifiable" and insert --identifiable--.

Column 7, line 48, delete "farther" and insert --further--.

Column 8, line 10, delete "indentifiable" and insert --identifiable--.

Column 8, line 36, delete "indentifiable" and insert --identifiable--.

Signed and Sealed this

Twelfth Day of May, 2009

JOHN DOLL
*Acting Director of the United States Patent and Trademark Office*